United States Patent
Chen et al.

(10) Patent No.: US 9,006,650 B2
(45) Date of Patent: Apr. 14, 2015

(54) DIRECT MEASUREMENTS OF NANOPARTICLES AND VIRUS BY VIRUS MASS SPECTROMETRY

(71) Applicant: Academia Sinica, Taipei (TW)

(72) Inventors: Chung-Hsuan Chen, Taipei (TW); Jung-Lee Lin, Taipei (TW); Huan Chang Lin, Taipei (TW)

(73) Assignee: Academia Sinica, Taipei (TW)

( * ) Notice: Subject to any disclaimer, the term of this patent is extended or adjusted under 35 U.S.C. 154(b) by 0 days.

(21) Appl. No.: 14/274,707

(22) Filed: May 10, 2014

(65) Prior Publication Data

US 2014/0346344 A1    Nov. 27, 2014

Related U.S. Application Data

(60) Provisional application No. 61/822,276, filed on May 10, 2013.

(51) Int. Cl.
*H01J 49/26* (2006.01)
*H01J 49/42* (2006.01)
*H01J 49/36* (2006.01)
*G01N 27/66* (2006.01)
*G01N 33/483* (2006.01)

(52) U.S. Cl.
CPC ............. *G01N 27/66* (2013.01); *H01J 49/36* (2013.01); *H01J 49/4225* (2013.01); *G01N 33/4833* (2013.01)

(58) Field of Classification Search
CPC ..... H01J 49/06; H01J 49/403; H01J 49/4225; H01J 49/4265; G01N 2560/00; G01N 27/66
USPC ................... 250/292, 282, 281, 287, 290
See application file for complete search history.

(56) References Cited

U.S. PATENT DOCUMENTS

| | | | | |
|---|---|---|---|---|
| 8,138,472 | B2 * | 3/2012 | Chen et al. | 250/282 |
| 2009/0189069 | A1 * | 7/2009 | Chen et al. | 250/282 |
| 2010/0301199 | A1 * | 12/2010 | Chen et al. | 250/282 |

* cited by examiner

*Primary Examiner* — Nikita Wells
(74) *Attorney, Agent, or Firm* — Eckman Basu LLP

(57) ABSTRACT

Apparatus and methods for performing mass spectrometry of a nanoparticle or virus analyte. Apparatus may include a laser desorption plate, a mass analyzer configured to measure mass over the range of m/z from $10^5$ to $10^{10}$, an electrical shield surrounding the mass analyzer, and a charge sensitive detector, wherein the laser firing is phase lock synchronized with the applied radiofrequency voltages.

26 Claims, 12 Drawing Sheets

DIRECT MEASUREMENTS OF NANOPARTICLES AND VIRUS BY VIRUS MASS SPECTROMETRY

BACKGROUND OF THE INVENTION

Viral infection is a major cause of disease and death throughout the world. To study and understand viruses and their diseases it is desirable to develop devices and methods for virus detection, characterization of viral growth and propagation, and quality control for nanoparticle production and other medical uses.

Viral disease can propagate in a cell or organism rapidly, and can be transmitted quickly and easily in many cases. Therefore, it is important to be able to rapidly measure and characterize the mass of a virus, a single whole virus, and virus particles.

Some methods for viral analysis include using a nanoscale cantilever beam operating as a mass detector, using a quartz crystal microbalance (QCM), using charge reduced electrospray size spectrometry, measuring discrete conductance changes characteristic of binding and unbinding, and microscopy-based mass spectrometry. Drawbacks of all of these methods include requiring a complex sample operation that is inconvenient for infectious materials. Thus, these methods have not achieved rapid and convenient detection at a single virus level.

It would be very useful to be able to detect and characterize viruses and virus particles by mass spectrometry. For example, it is desirable to measure and characterize viruses such as human immunodeficiency virus (HIV), flu viruses, and SARS virus, among many others.

Currently, mass spectrometers are limited to detecting analytes with m/z much lower than $10^8$. Commercial mass spectrometers typically use a charge amplification device such as a channeltron, electromultiplier or microchannel plate (MCT) for detection. A charge amplification device does work well with the m/z of the charged particle higher than about $10^5$ to $10^6$.

It has been shown that detecting both m/z and z of a single microparticle can be done at the same time using a mass spectrometer which can measure charge directly. The mass of a microparticle or cell could be obtained. In general, when z and m/z can be correctly obtained, the mass (m) can be revealed. The mass of a microparticle or cell could be obtained.

The mass distribution of cells or microparticles could be determined by measuring mass-to-charge ratios (m/z) and charge (z) simultaneously.

One drawback to this approach is that the number of charges on each particle needs to be high, because electronic charge measurement devices have an electronic background noise of about 50 to 500 electrons. When the number of charges on the particle to be measured is less than about 500, it is difficult to obtain the correct mass.

Most cells or microparticles in a vacuum have more than 1000 charges.

Another drawback to this approach is that to obtain the correct z, only one cell or one particle can be measured by the detector at any one time.

Because of these drawbacks, this approach cannot be applied to the measurement of a nanoparticle or virus. For example, a nanoparticle or a virion typically has less than 500 charges so that the mass cannot be determined accurately due to the electronic background.

It is also difficult to quickly measure the masses of nanoparticles. One approach is to use electron microscopy to measure the size of a nanoparticle and calculate the mass based on the density. However, this is a tedious and very time-consuming approach.

There is a continuing need for apparatus and methods for rapidly measuring the masses of nanoparticles, detecting a virus, a nanoparticle, a single whole virus, a virion, or a virus particle using mass spectrometry.

BRIEF SUMMARY OF THE INVENTION

This invention relates to the fields of virus detection, virus characterization, and mass spectrometry. More particularly, this invention relates to detection and characterization of a virus, a single whole virus, and virus particles using mass spectrometry.

This invention encompasses methods and apparatus for virus detection, virus characterization, and mass spectrometry. More particularly, this invention relates to detection and characterization of a virus, a single whole virus, and virus particles using mass spectrometry.

This invention provides apparatus and methods for measuring the mass and mass distributions of nanoparticles and viruses. In some embodiments, this invention provides for mass measurement methods in the mass region of a nanoparticle or virus of 1 MDa to 1 GDa. In certain embodiments, this disclosure provides a nanoparticle/virus mass spectrometry technique to make rapid and accurate mass and mass distribution measurements of nanoparticles and viruses. Among other things, this technique can be used for the identification of viruses, or to monitor drug delivery when nanoparticles are used as carriers.

Embodiments of this invention include:

An apparatus for mass spectrometry comprising:

a desorption plate;

a laser for firing a beam to impinge upon the desorption plate;

a mass analyzer for measuring mass over the range of m/z from $10^5$ to $10^{10}$ using applied trapping RF and axial RF voltages, wherein the mass analyzer is a quadrupole ion trap having a ring electrode and first and second end cap electrodes, wherein the ring electrode is spaced apart by a gap from the first end cap electrode, and wherein the desorption plate is adjacent to the gap;

an electrical shield surrounding the mass analyzer;

a charge sensitive detector, wherein the electrical shield electrically isolates the mass analyzer from the charge sensitive detector; and a synchronizer for phase locking the laser firing to the applied trapping RF.

The apparatus above, wherein a trapping RF is applied to the ring electrode, and an axial RF is applied to the end cap electrodes, and wherein the phase of the trapping RF is synchronized to the phase of the axial RF. The apparatus above, wherein the resolution of a mass spectrum of nanoparticles obtained with the apparatus is at least 50. The apparatus above, wherein the laser fires when the applied radiofrequency voltage amplitude is less than one volt. The apparatus above, wherein the laser fires when the applied radiofrequency voltage amplitude is zero. The apparatus above, wherein the desorption plate is a laser induced acoustic desorption plate.

The apparatus above, wherein the mass analyzer is a quadrupole ion trap. The apparatus above, wherein the applied radiofrequency voltages are applied at a trap driving frequency in the range 200-2000 Hz. The apparatus above, wherein the applied radiofrequency voltages are in the range zero to 3000 Vp-p.

The apparatus above, wherein the electrical shield is stainless steel.

A method for performing mass spectrometry of a nanoparticle analyte ion, the method comprising:

desorbing the nanoparticle analyte ion from an acoustic desorption plate by firing a laser to impinge upon the desorption plate;

trapping the nanoparticle analyte ion in a mass analyzer configured to measure mass over the range of m/z from $10^5$ to $10^{10}$ using applied trapping RF and axial RF voltages, wherein the mass analyzer is a quadrupole ion trap having a ring electrode and first and second end cap electrodes, wherein the ring electrode is spaced apart by a gap from the first end cap electrode, and wherein the desorption plate is adjacent to the gap; and detecting the charge of the nanoparticle analyte, wherein an electrical shield electrically isolates the mass analyzer from the detector, thereby obtaining a mass spectrum of the analyte;

and wherein the laser firing is phase lock synchronized to the applied trapping RF.

The method above, the method further comprising
applying a trapping RF to the ring electrode and an axial RF to the end cap electrodes; and
synchronizing the phase of the trapping RF to the phase of the axial RF.

The method above, further comprising adjusting the phase of the RF at which the laser is fired, thereby increasing the signal to noise. The method above, wherein the laser fires when the applied radiofrequency voltage amplitude is less than one volt. The method above, wherein the laser fires when the applied radiofrequency voltage amplitude is zero.

The method above, wherein the signal to noise of the mass spectrum is increased at least two-fold compared to a device that does not have phase synchronized laser firing.

The method above, wherein the nanoparticles are viruses. The method above, wherein the nanoparticles are single whole viruses. The method above, wherein the nanoparticles are virions. The method above, wherein the nanoparticles are nanorods, quantum dots, liposomes, or multiple layers of nanoparticles. The method above, wherein the nanoparticles are human immunodeficiency virus, flu virus, or SARS virus. The method above, wherein the mass distribution of the nanoparticles is determined.

The method above, further comprising matching the peaks in the mass spectrum of the nanoparticles with different charges and/or clusters with different numbers of charge. The method above, further comprising determining the kinds of viruses present in a sample based on mass measurements.

A non-transient computer readable storage medium containing instructions for carrying out a method for performing mass spectrometry of a nanoparticle analyte ion, the method comprising:

desorbing the nanoparticle analyte ion from an acoustic desorption plate by firing a laser to impinge upon the desorption plate;

trapping the nanoparticle analyte ion in a mass analyzer configured to measure mass over the range of m/z from $10^5$ to $10^{10}$ using applied radiofrequency voltages, wherein the mass analyzer is a quadrupole ion trap having a ring electrode and first and second end cap electrodes, wherein the ring electrode is spaced apart by a gap from the first end cap electrode, and wherein the desorption plate is adjacent to the gap; and detecting the charge of the nanoparticle analyte, wherein an electrical shield electrically isolates the mass analyzer from the detector;

and wherein the laser firing is phase lock synchronized to the applied radiofrequency voltages.

The non-transient computer readable storage medium above, the method further comprising
applying a trapping RF to the ring electrode and an axial RF to the end cap electrodes; and
synchronizing the phase of the trapping RF to the phase of the axial RF.

BRIEF DESCRIPTION OF THE DRAWINGS

FIG. 2a shows the spectrum obtained without a phase lock system, and FIG. 2b shows the spectrum obtained with a phase lock system.

FIG. 3a, 50 nm, 2000 Hz and 1000V, FIG. 3b, 100 nm, 1500 Hz and 1000V. The masses of particles were measured. The scan time was 100 ms.

FIG. 4a shows the mass spectrum of HIV measured by VMS. The typical trapping parameters (Ω/2π and Vp-p) used in each measurement were 1500 Hz and 1000V. The scan time was 100 ms. FIG. 4b shows a chart of measured masses versus assigned particle numbers for HIV. Upper inset: electron micrographs of HIV. Lower inset: schematic of the single HIV structure. In FIG. 4, the accuracy of the mass measurement is about 1%, and the resolution is about 2%. Therefore, the observed mass variety should exhibit the mass distribution of the virus particles. This is a rapid and reliable measurement of both the mass of a nanoparticle/virus and its mass distribution.

FIG. 5a shows H1N1. FIG. 5b shows H3N2. FIG. 5c shows H5N1. The typical trapping parameters (Ω/2π and Vp-p) used in each measurement were 1500 Hz and 1000V. The scan time was 100 ms.

Figure 8:
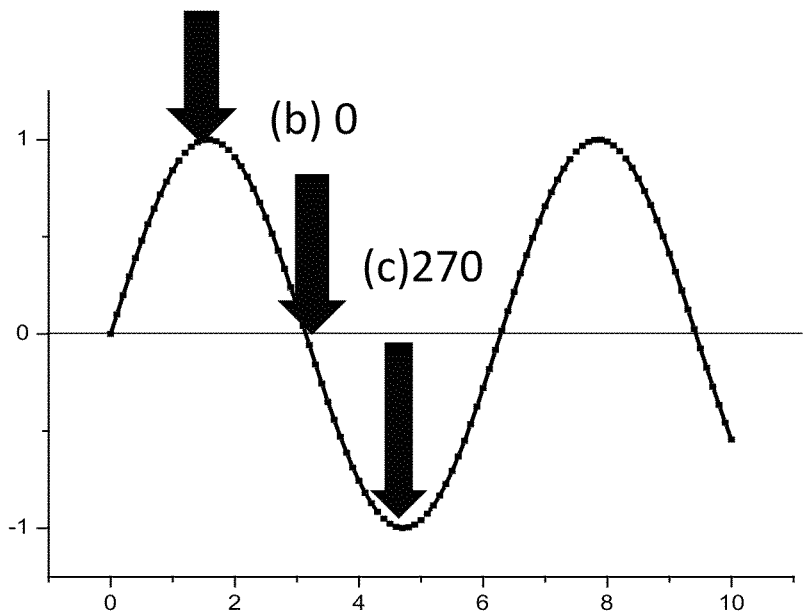

FIG. 8 shows a timing diagram for an embodiment of a method of this invention. When the laser is fired on the 90 degree phase of the trapping RF, ions are in general not trapped. When the laser is fired on the 0 degree phase of the trapping RF, many ions are trapped. When the laser is fired on the 270 degree phase of the trapping RF, ions are in general not trapped.

Figure 9:
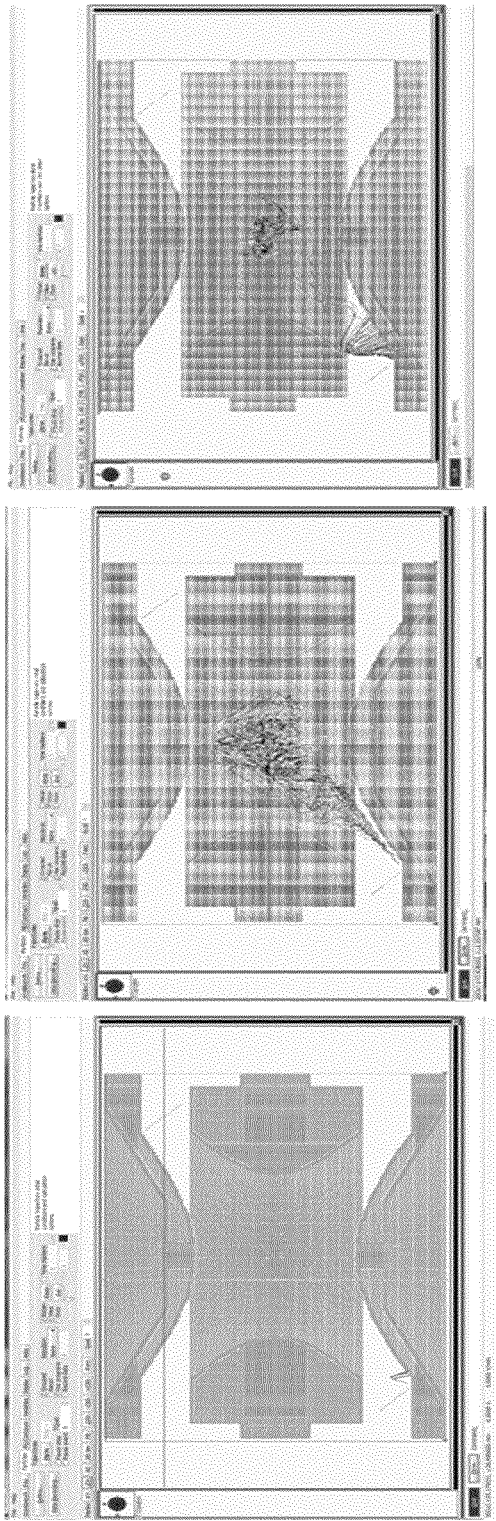

FIG. 9 shows the results calculated for entry of ions into the trap in an apparatus or method of this invention. When the laser is fired at the 90 degree phase position, few ions enter and are held in the trap, and the ions can be repelled to the end cap. When the laser is fired at the 0 degree phase position, many ions can pass through the gap to the center of the ion trap. When the laser is fired at the 270 degree phase position, few ions enter the trap, and ions can be repelled to the end cap.

Figure 10:
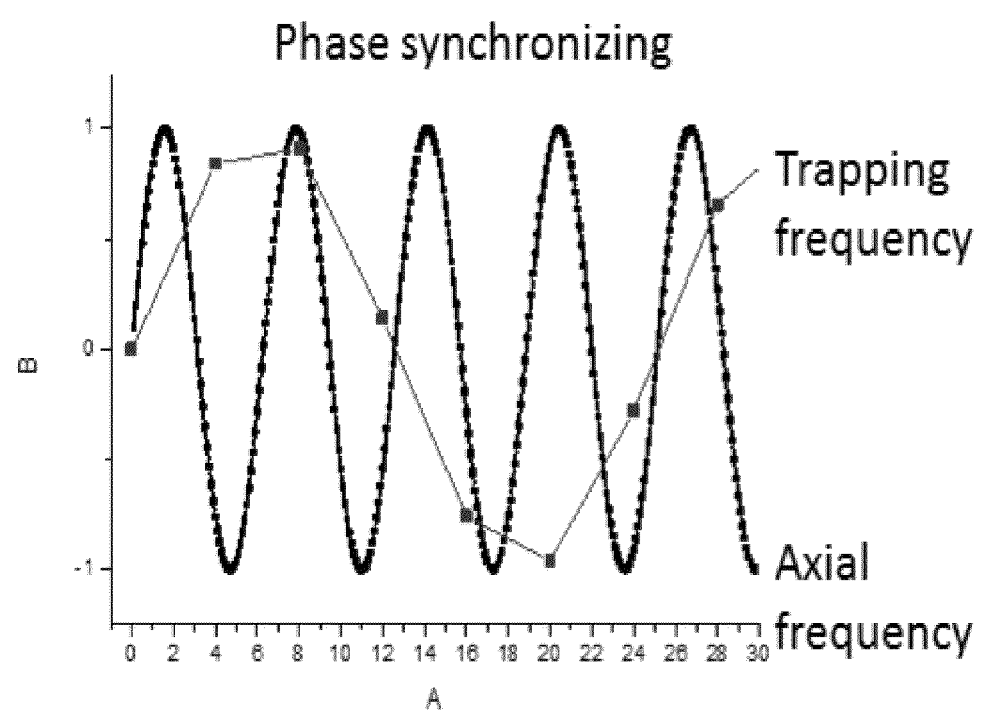

FIG. 10 shows a timing diagram for the synchronization of the trapping RF and the axial RF.

Figure 11:
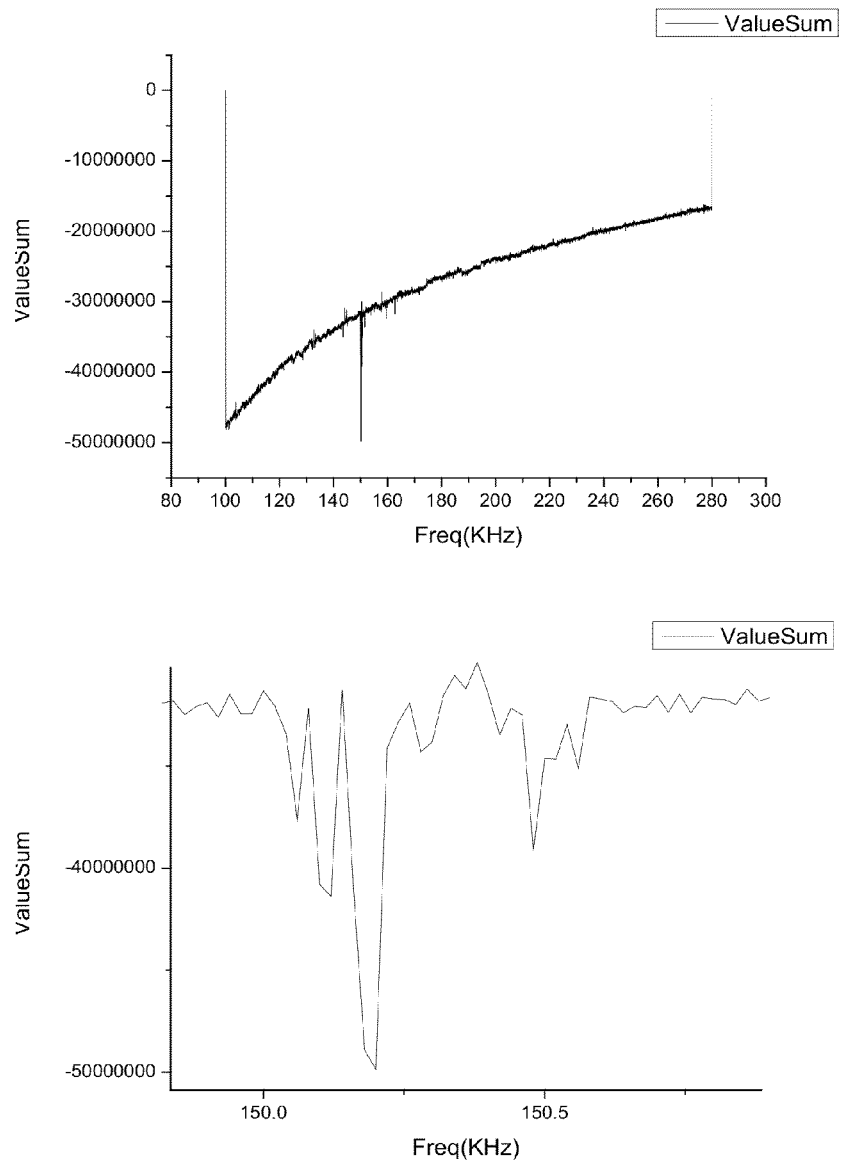

FIG. 11 shows the mass spectrum of C60 nanoparticles obtained by a mass spectrometer apparatus of this invention. The main peak that was observed shows that m/z 720 was detected, along with m/z 721 and m/z 722.

Figure 12:
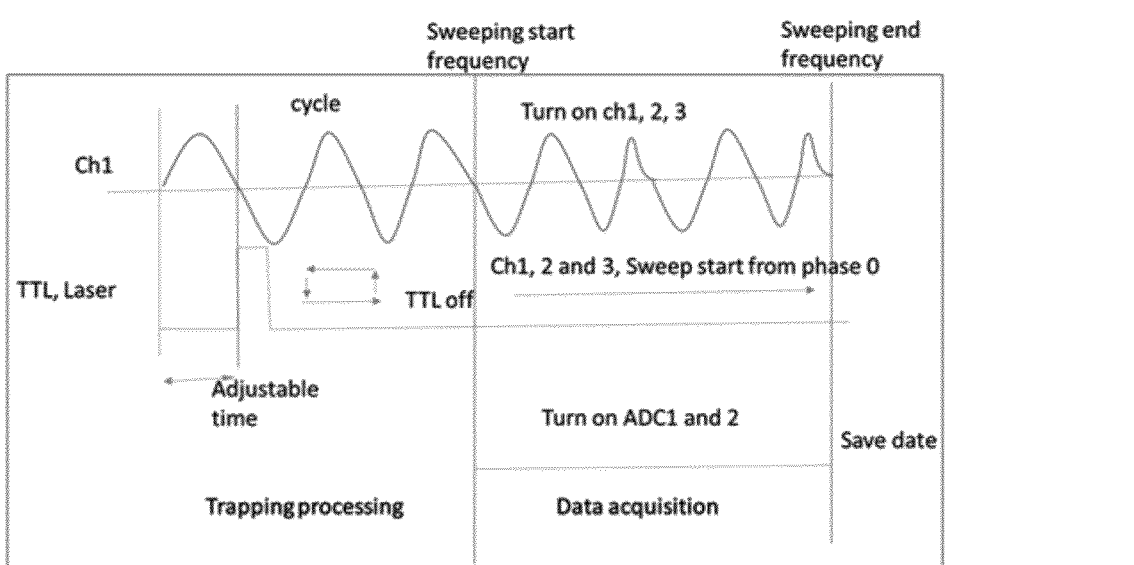

FIG. 12 shows a timing diagram for frequency sweeping and signal acquisition in embodiments of this invention. The trapping RF and axial RF are synchronized to increase the resolution in the mass spectrum.

DETAILED DESCRIPTION OF THE INVENTION

Embodiments of this invention provide apparatus and methods for virus detection and virus characterization using mass spectrometry. In some embodiments, this invention provides apparatus and methods for mass spectrometry to detect and characterize a virus, a single whole virus, and virus particles.

Mass spectrometry can be used to measure the mass-to-charge ratio (m/z) of a particle such as an atom, a molecule or a cluster. For an atomic ion or a small molecular ion, the number of charges (z) is often equal to 1, so that the mass-to-charge ratio (m/z) is the same as m.

In contrast, for a microparticle or a cell, the number of charges can be many thousands or more.

Embodiments of this invention provide an apparatus for mass spectrometry that can be used to measure the mass-to-charge ratio (m/z) of a nanoparticle or virion. With this approach, the total charges of several particles with the same m/z can be measured. The m/z for different sizes of nanoparticles, virions, or virion clusters can also be measured.

This disclosure provides methods to measure the mass and mass distributions of nanoparticles/viruses. In some embodiments, a nanoparticle/virus mass spectrometry technique is provided to make rapid and accurate mass and mass distribution measurements of nanoparticles/viruses. The apparatus and methods of this disclosure are useful for the quality control of nanoparticle production, as well as the identification of various viruses. Further, they can be to measure the degree of infection by measuring the number of viruses in specific cells or in plasma.

In certain embodiments, an apparatus for mass spectrometry is configured to obtain the mass of a nanoparticle or virion. In general, the minimum difference for z is one, and the minimum difference in cluster size is one nanoparticle or virion. Thus, an apparatus for mass spectrometry of this invention can obtain the mass of the nanoparticle or virion by data fitting.

In some embodiments, this invention provides an apparatus and method for the measurement and characterization of nanoparticles or virions.

Embodiments of this invention provide an apparatus to measure the total charge of different particles having the same m/z. The apparatus may also measure m/z for different sizes of nanoparticles, virions or virion clusters.

An apparatus and method of this invention can obtain the mass of the nanoparticle/virion by data fitting.

Differences between an apparatus of this invention and conventional ESI for large biomolecule detection include using laser-induced acoustic desorption (LIAD) to desorb the samples as compared to ESI which is a spray process.

Further, an apparatus of this invention has a mass analyzer configured to analyze ions with m/z higher than $10^8$. No conventional mass spectrometer can measure m/z in this region.

Moreover, an apparatus of this invention may use direct charge measurement.

Embodiments of this invention can be used to measure the mass of viruses, including HIV and different kinds of flu viruses.

In some embodiments, an apparatus of this invention may have a laser induced desorption ionization source, or a LIAD ionization source. A laser induced desorption ionization source advantageously provides desorption without a matrix compound, such as may be used in MALDI and ESI methods. A laser induced desorption ionization source advantageously allows desorption of intact bioparticles including viruses, bacteria, and whole mammalian cells. A laser induced desorption ionization source advantageously avoids interaction of a matrix compound with the viruses or nanoparticles to be detected. A laser induced desorption ionization source advantageously avoids interference with the measured viruses or nanoparticles by the desorbed matrix particles.

In some aspects, this invention provides rapid measurement of the mass of virus or nanoparticles, where the mass is below about $1 \times 10^{12}$ Da, or below about $1 \times 10^{13}$ Da.

Figure 1:
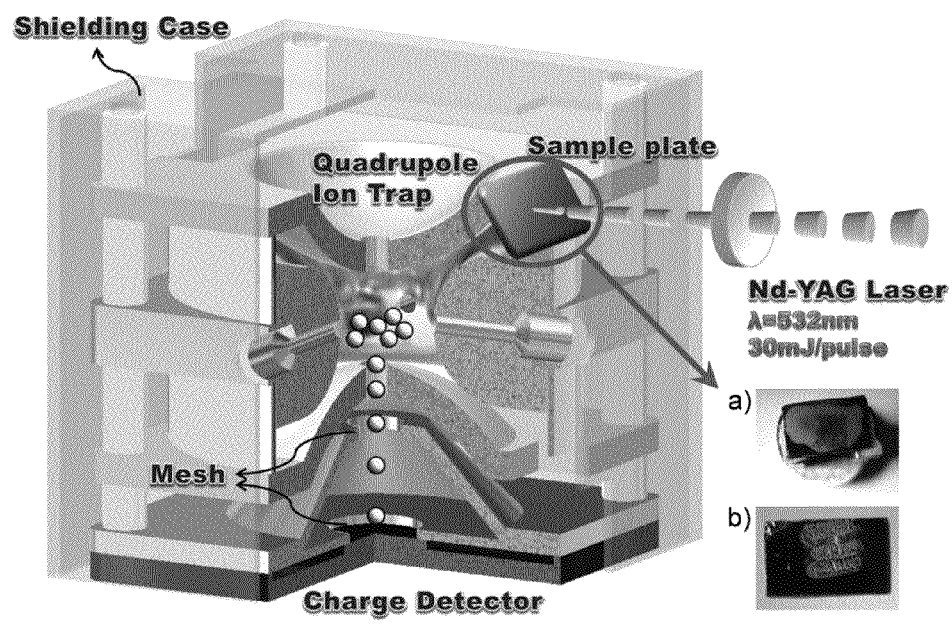
FIG. 1 shows a schematic of an embodiment of a Virus Mass Spectrometer (VMS) of this invention. The VMS includes a quadrupole ion trap, a pulsed Nd:YAG laser, a charge detector, a stainless steel shielding case, and $SiO_2$ sample plate (400 nm thickness, High Resistance surface). Inset (a) shows an aliquot (10 μL) of purified particle in front side of sample plate. Inset (b) shows a frequency-doubled Nd:YAG laser beam (λ=532 nm, 30 mJ/pulse) with a pulse duration of approximately 6 ns was shone directly onto the back side of sample plate.

An embodiment of an apparatus of this invention is shown in FIG. 1. In FIG. 1, the sample plane (for example, a 10 mm×5 mm, 400 µm thick silicon wafer) was positioned in the gap between the ring and endcap electrodes (for example, $2r_0$=19.97±0.02 mm) of the quadrupole ion trap (QIT). A frequency-doubled pulsed Nd:YAG laser at 532 nm with a laser energy at 30 mJ/pulse was used to irradiate the sample from the back side of the silicon wafer and damped to the trap center by helium gas at about 60 mTorr. The Nd:YAG laser at 532 nm impinges upon the back of sample plane.

In the inventive apparatus of FIG. 1, the particles in the ion trap would not remain trapped if the laser was to be fired during the application of high radio-frequency (RF) voltage.

In the inventive apparatus of FIG. 1, which may be called a virus mass spectrometer (VMS), a shielding reduces the noise of the charge detector. The shielding may be integrated with the mass analyzer. The shielding may be a case of stainless steel. Further, in operation, the time of the laser firing is controlled or phase synchronized so that it occurs at low or zero RF voltage. Surprisingly, this increases trap efficiency so that more nanoparticles are collected.

In some embodiments, the laser firing is controlled or phase synchronized so that it occurs at less than one volt RF voltage. This increases trap efficiency by an unexpectedly advantageous amount, so that more nanoparticles are collected. In some embodiments, the laser firing is controlled or phase synchronized so that it occurs at less than 500 millivolts RF voltage. In some embodiments, the laser firing is controlled or phase synchronized so that it occurs at less than five volts RF voltage. In some embodiments, the laser firing is controlled or phase synchronized so that it occurs at less than ten volts RF voltage.

A quadrupole ion trap maintains ions in stable trajectories within the trap using a trapping radio frequency (RF) voltage applied to the ring electrode. The ion trajectories can be made unstable in a mass-selective manner, also called resonance ejection, using an auxiliary axial RF voltage applied to the end cap electrodes, so that the quadrupole ion trap can be used as a mass analyzer.

Embodiments of this invention provide an ion trap that can be operated under an axial mass-selective instability mode by scanning the trapping frequency in the range 2000-200 Hz. A voltage of 1000 Vpp can be initially applied with a high-voltage transformer driven by an RF voltage power amplifier and a function generator. The frequency can be scanned with the function generator so that particles with an unstable trajectory can be ejected along the axial direction, and detected with a charge detector.

In operating an inventive apparatus of this invention, the phase of the trapping RF voltage and the phase of the auxiliary axial RF voltage can be phase synchronized.

To synchronize the phases of the trapping RF voltage and the auxiliary axial RF voltage, the waveforms of both the trapping and axial resonance frequencies can be generated with a digitized arbitrary function generator. Software generated waveform tables can be downloaded to the memory of a digitalized arbitrary function generator.

Thus, the phases of the trapping RF voltage and the auxiliary axial RF voltage can be synchronized to each other, as well as to the laser firing, even as the frequency of the RF is being swept. This synchronization during frequency sweeping achieves the advantage of increased analyte signal.

In further aspects, synchronizing the trapping RF to the axial RF can surprisingly increase the resolution of the mass spectrum. The resolution of the mass spectrum can be increased when ion ejection is performed under synchronizing conditions. The bandwidth of m/z that is ejected from the ion trap can be narrowed when synchronizing the trapping RF to the axial RF. This method can increase the resolution of m/z in the mass spectrum.

In operation, the end-cap electrodes can be grounded during a linear sweep scan of the trapping RF voltage.

In operation, the end-cap electrodes can be connected to an auxiliary waveform generator in order to perform resonance ejection. During a resonance frequency sweep, the phase of the trapping frequency can be synchronized with that of the auxiliary waveform.

In operation, the laser firing can be synchronized with the phase of the applied RF voltages, thereby increasing the trapping efficiency.

The laser firing can be synchronized with the zero radio frequency (RF) voltage with a four channel digital delay/pulse generator (Stanford Research System, Inc., DG535). With this approach, the analysis speed can be increased by a factor of at least about 10.

In some aspects, a shielding can be provided to the charge detector to reduce the electronic background.

In certain embodiments, laser desorption of nanoparticles and viruses can be performed without any matrix.

In general, an inventive apparatus of this disclosure can rapidly measure the mass of a virus or nanoparticle. For example, with an apparatus configured as a VMS instrument, the time required for a mass measurement for a virus can be reduced by orders of magnitude relative to microscopy-based mass spectrometry. In some embodiments, the time required for a mass measurement for a virus with an apparatus configured as an inventive VMS instrument of this disclosure can be less than 20 minutes, or less than 10 minutes, or less than 5 minutes, or less than 3 minutes, or less than 1 minute.

An inventive apparatus of this disclosure can measure the mass of a virus or nanoparticle with surprisingly increased signal to noise ratio, relative to a device that does not have phase synchronized laser firing. In some embodiments, the signal to noise of the mass spectrum is increased at least two-fold. In certain embodiments, the signal to noise of the mass spectrum is increased at least five-fold. The increased signal to noise provided by an inventive apparatus of this disclosure can surprisingly reduce the time required for a mass measurement of a virus, microparticle, or nanoparticle.

In certain embodiments, phase lock control is employed to enhance trapping efficiency and collect more and more particles of the ion trap. Phase lock synchronization links the timing of the laser firing to the phase of the RF applied. In phase lock control, the laser firing is timed to occur at low or zero RF voltage. Phase lock control can be performed with, for example, a four channel digital delay pulse generator.

In some aspects, a virus mass spectrometer of this invention can include laser induced acoustic desorption for desorbing virion/nanoparticle into a mass analyzer, a mass analyzer which can cover the region of m/z from $10^5$ to $10^{10}$, a charge sensitive detector, and phase synchronization for RF and laser firing time so that the laser fires when the RF amplitude is low or zero.

In some aspects, this disclosure describes a method for determining the mass of a virion/nanoparticle by matching the peaks of a particle with different charges and/or clusters with different numbers of charge.

In some aspects, this disclosure describes that a VMS apparatus can be used to measure different types of nanoparticles and different shapes of nanoparticles such as nanorod, quantum dots, liposome and multiple layers of nanoparticles.

In some aspects, this disclosure describes an apparatus and method for rapidly determining the types or kinds of virus present in a sample based on mass measurements.

In some aspects, this disclosure describes an apparatus and method for rapidly measuring the masses of nanoparticles and their mass distributions.

The ion trap can be operated under an axial mass-selective instability mode by scanning the trapping frequency in the range 2000-200 Hz. A voltage of 1000 Vpp can be initially applied with a high-voltage transformer driven by an RF voltage power amplifier (TReK, Inc., Model 5-80) and a function generator (DG345). The frequency can be scanned with a functional generator so that particles with an unstable trajectory can be ejected along the axial direction and subsequently detected by a charge detector. This instrument can rapidly measure the mass of a nanoparticle or virus and a microparticle or cell. On average, the measurement of one sample can require less than 1 min.

Some descriptions of apparatus and methods can be found in "High-Speed Mass Measurement of Nanoparticle and Virus," Anal. Chem. 2012, 84, 4965-4969, Huan-Chang Lin, et al., which is hereby incorporated by reference for all purposes.

EXAMPLE 1

Figure 2:
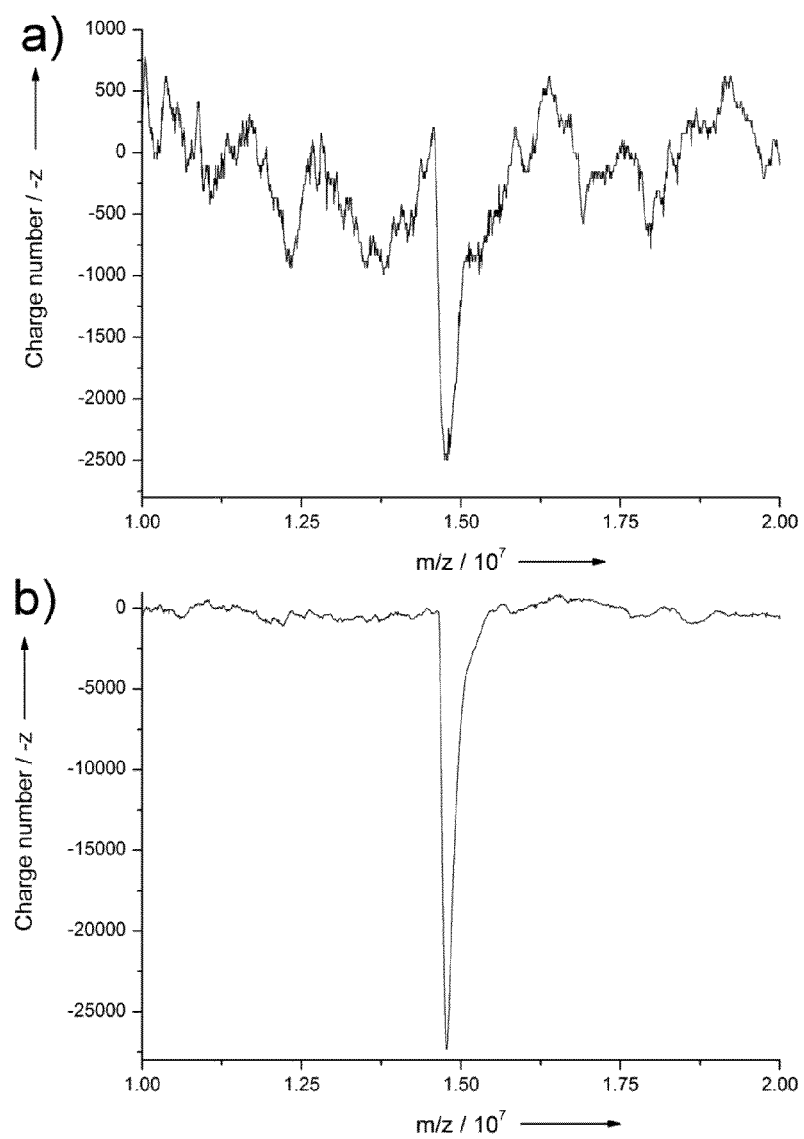
FIG. 2 shows examples of single-scan mass spectra of 50 nm polystyrene sphere particles obtained using a Virus Mass Spectrometer.

As shown in FIG. 2, synchronizing the time of the laser firing so that it occurs at zero RF voltage increases trap efficiency so that more nanoparticles are collected. In FIG. 2, the mass spectrum of 50 nm polystyrene sphere particles (Thermo Scientific) was obtained with an apparatus configured as an inventive VMS instrument of this disclosure. The single-scan mass spectra of 50 nm polystyrene sphere particles with the inventive VMS instrument were obtained: (a) without phase synchronization, and (b) with phase synchronization. Surprisingly, the signal to noise of the mass spectrum is greatly increased.

EXAMPLE 2

Figure 3:
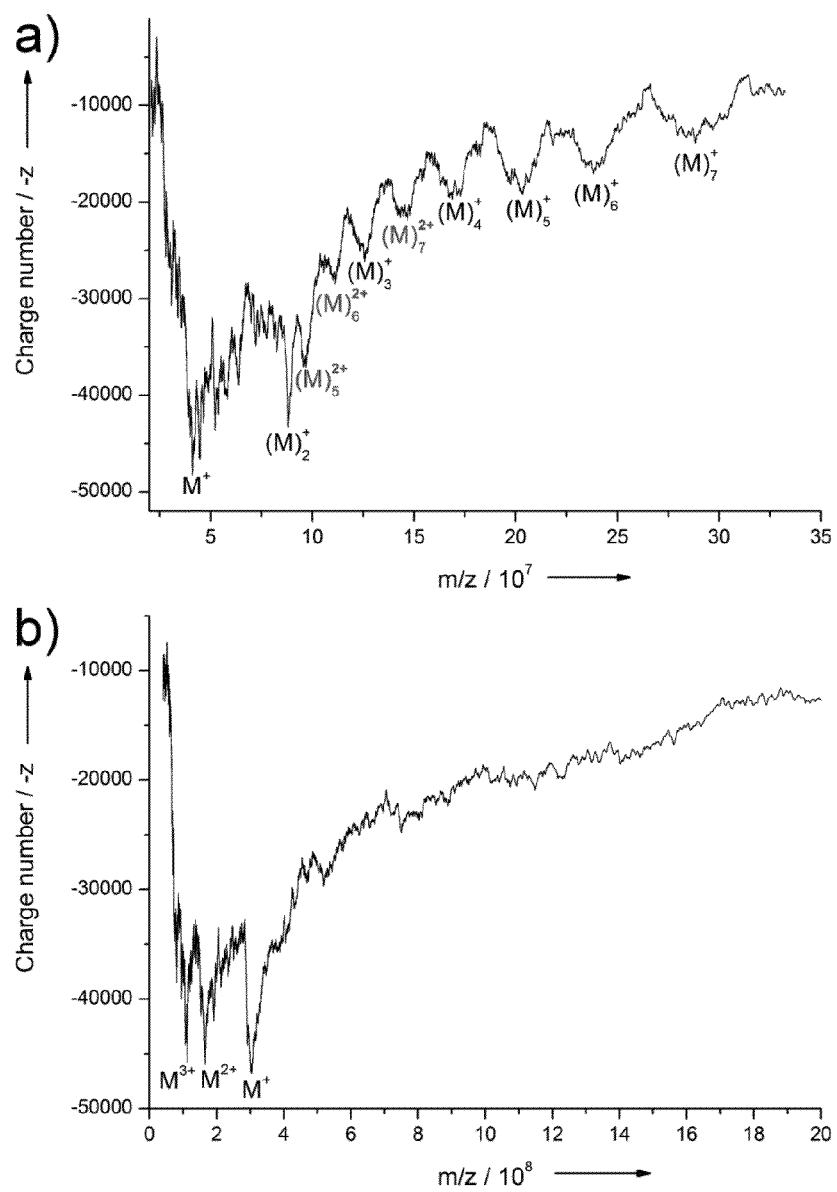
FIG. 3 shows mass spectra of 50 nm and 100 nm polystyrene sphere particles obtained using a Virus Mass Spectrometer. The trapping parameters (Ω/2π and Vp-p) used in each measurement were.

With an apparatus configured as an inventive VMS instrument of this disclosure, the masses of virus were detected accurately. In this example, polystyrene spheres (Thermo Scientific) with sizes of 50 and 100 nm were detected. The mass spectrum of these polystyrene sphere particles by VMS is shown in FIG. 3. These masses were close to the mass range of a virus. The calculated masses were $4.14 \times 10^7$ and $3.3 \times 10^8$ Da, respectively. The ion trap was operated under an axial mass-selective instability mode by scanning the trap driving frequency in the range 2000-500 Hz and 1500-200 Hz, respectively. A voltage of 1000 Vp-p was initially applied with a high-voltage transformer driven by a RF voltage power amplifier and a functional generator. In scanning the frequency, the scanning rate window is fixed at 100 ms with the functional generator, and particles could be ejected along an axial direction and subsequently detected with a charge sensitive detector. All of the mass spectra were the sum of twenty single-scan mass spectra.

In some embodiments, the ion trap was operated under an axial mass-selective instability mode by scanning the trap driving frequency in the range 2000-500 Hz and the axial frequency in the range 1500-200 Hz.

EXAMPLE 3

In FIG. 3a, the m/z of 50 nm polystyrene sphere particles were measured to be $4.12 \times 10^7$ ($M^+$, monomer), $8.6 \times 10^7$ ($M^{2+}$, dimer), $1.26 \times 10^8$ ($M^{3+}$), $1.68 \times 10^8$ ($M^{4+}$), $2.04 \times 10^8$ ($M^{5+}$), $2.47 \times 10^8$ ($M^{6+}$), and $2.88 \times 10^8$ ($M^{7-}$). The particle numbers were determined by dividing intensity of charge sensitive detector and charge number of particle. The clusters carried double charges and were measured to be $9.8 \times 10^7$ ($M_5^{2+}$), $1.19 \times 10^8$ ($M_6^{2+}$), and $1.46 \times 10^8$ ($M_7^{2+}$). These results show that larger nanoparticles carry more charges when the volume of the particles (larger clusters) increases. These results agree with the calculated mass of 50 nm polystyrene sphere monoparticles ($4.14 \times 10^7$ Da).

In FIG. 3b, the m/z of 100 nm polystyrene sphere particles were measured to be $3.26 \times 10^8$ ($M^+$, single charge), $1.65 \times 10^8$ ($M^{2+}$, double charges), and $1.12 \times 10^8$ ($M^{3+}$, triple charges). These are in agreement with the calculated mass of 100 nm polystyrene sphere monoparticles as $3.3 \times 10^8$ Da. For these experiments, the mass spectra of 50 nm and 100 nm polystyrene sphere particles were obtained by VMS. The typical trapping parameters ($\Omega/2\pi$ and Vp-p) used in each measurement were FIG. 3a, 50 nm, 2000 Hz and 1000 V, FIG. 3b, 100 nm, 1500 Hz and 1000 V. The mass of 100 nm polystyrene sphere monoparticles was measured to be $3.53 \times 10^8$ Da which agrees with the calculated mass of $3.3 \times 10^8$ Da. The scan time was 100 ms.

EXAMPLE 4

The mass of HIV based lentivirus was measured with an apparatus configured as an inventive VMS instrument of this disclosure. HIV is a spherical enveloped virus, about 90-120 nm in diameter with a three layer structure and the virion buoyant density is 1.16-1.18 g/cm$^3$ in sucrose. The m/z of HIV lentivirus was measured to be $3.53 \times 10^8$ ($M^+$, monomer), $7.12 \times 10^8$ ($M^{2-}$, dimer), and $1.08 \times 10^9$ ($M^{3+}$, trimer). The clusters carried multi-charges were measured to be $5.2 \times 10^8$ ($M_3^{2+}$), $2.7 \times 10^8$ ($M_3^4$), and $2.1 \times 10^8$ ($M_3^{5+}$) as shown in FIG. 4a. These results agree with the calculated mass range of single HIV lentivirus from $2.67 \times 10^8$ to $6.43 \times 10^8$ Da, depending on diameter (90-120 nm) and density (1.16-1.18 g/cm$^3$) in HIV spherical virus. In FIG. 4b, the accuracy of the mass measurement by VMS was better than 1%, the observed mass variety exhibited the constitutional mass range of virus particle.

Figure 4:
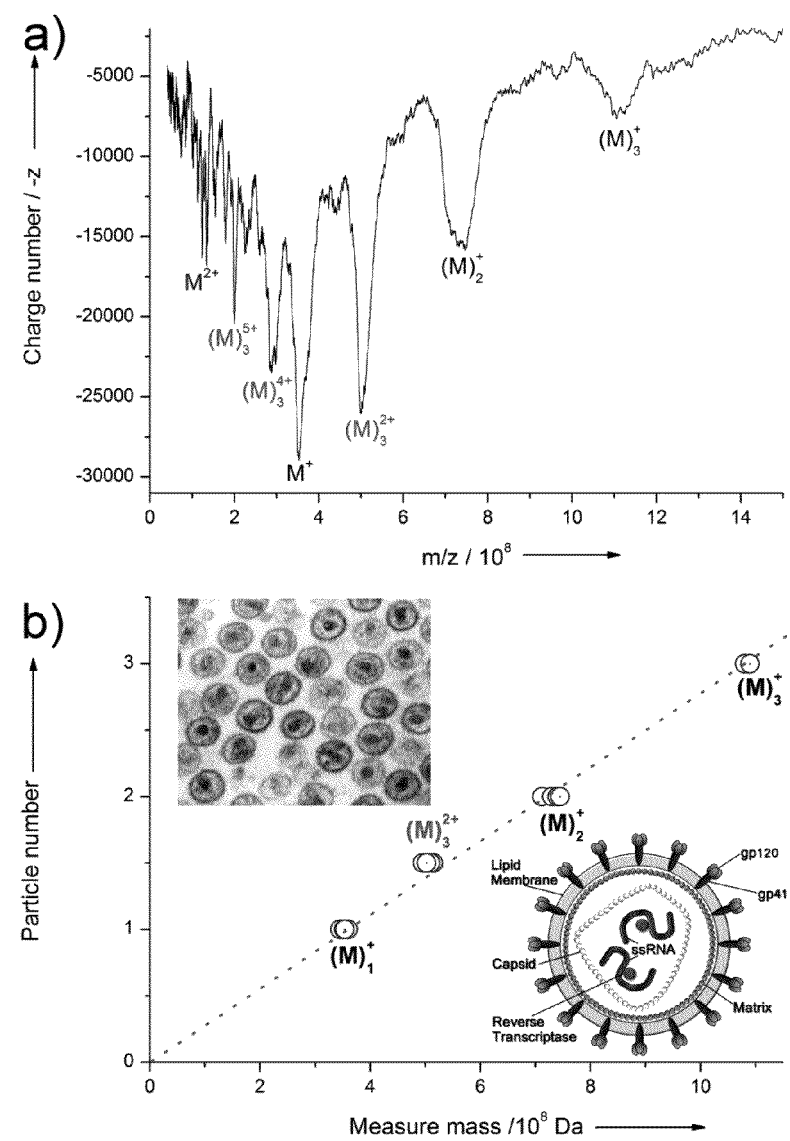
FIG. 4 shows mass spectra of HIV using a Virus Mass Spectrometer.

In FIG. 4, the accuracy of the mass measurement is about 1%, and the resolution is about 2%. Therefore, the observed mass variety should exhibit the mass distribution of the virus particles. This is a rapid and reliable measurement of both the mass of a nanoparticle/virus and its mass distribution.

EXAMPLE 5

Figure 5:
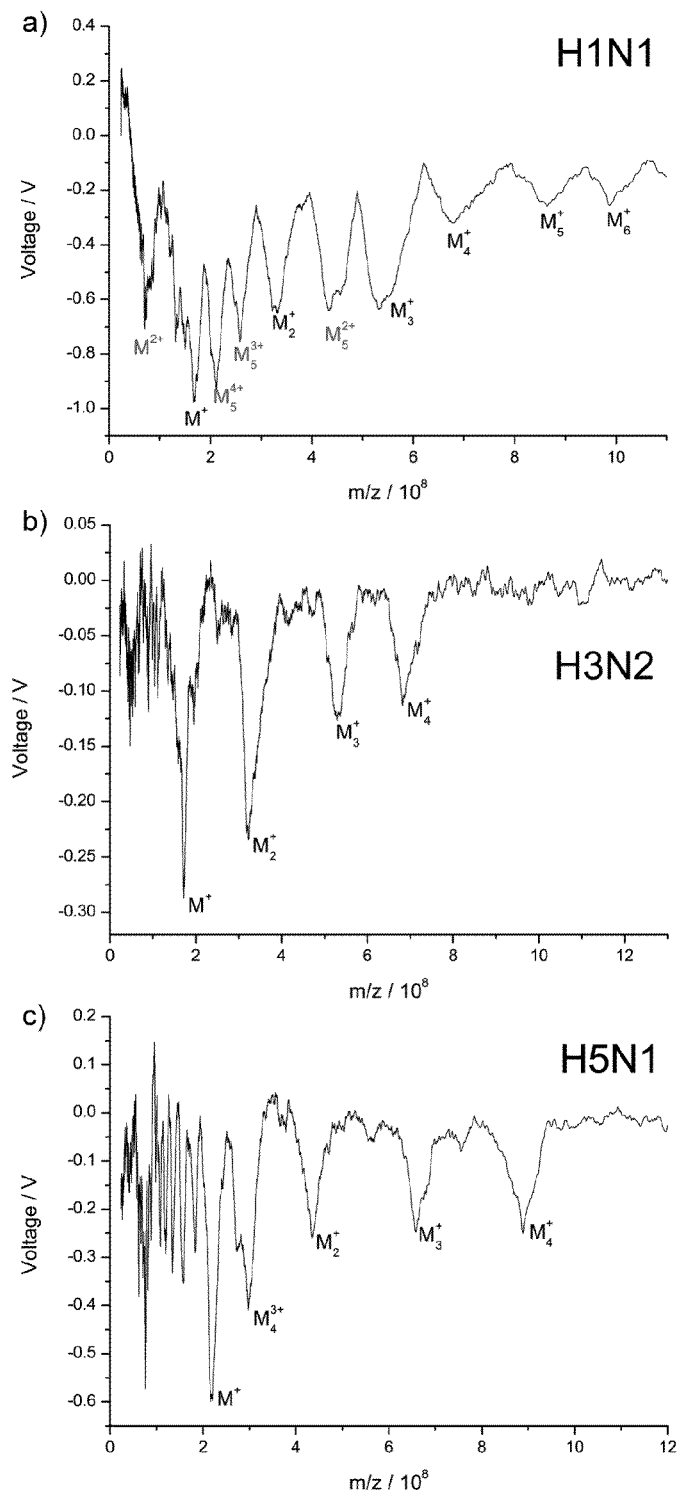
FIG. 5 shows the mass spectrum of influenza virus measured by VMS.

The mass of influenza virus was measured with an apparatus configured as an inventive VMS instrument of this disclosure. The influenza viruses were H1N1, H3N2, and H5N1. The m/z of H1N1 was measured to be $1.7 \times 10^8$ ($M^+$, monomer), $3.4 \times 10^8$ ($M^{2+}$, dimer), $5.3 \times 10^8$ ($M^{3+}$, trimer), $6.8 \times 10^8$ ($M^{4+}$), $8.5 \times 10^8$ ($M^{5+}$), and $1.0 \times 10^9$ ($M^{6+}$). The m/z for clusters carried multi-charges were measured to be $4.3 \times 10^8$ ($M_5^{2+}$), $2.5 \times 10^8$ ($M_5^{3+}$), and $1.7 \times 10^8$ ($M_5^{4+}$). These results are shown in FIG. 5a. The m/z of H3N2 was measured to be $1.7 \times 10^8$ ($M^+$, monomer), $3.3 \times 10^8$ ($M^{2+}$, dimer), $5.2 \times 10^8$ ($M^{3+}$, trimer), and $6.8 \times 10^8$ ($M^{4+}$). The results are shown in FIG. 5b. The m/z of H5N1 was measured to be $2.2 \times 10^8$ ($M^+$, monomer), $4.4 \times 10^8$ ($M^{2-}$, dimer), $6.5 \times 10^8$ ($M^{3-}$, trimer), and $8.9 \times 10^8$ ($M^{4+}$). The clusters carried multi-charges were measured to be $2.9 \times 10^8$ ($M_4^{3+}$). The results are shown in FIG. 5c.

EXAMPLE 6

Operation of an apparatus configured as an inventive VMS instrument of this disclosure is described. An inventive VMS instrument may include a desorption plate for laser-induced acoustic desorption or LIAD of virus and nanoparticles without any matrix. Virus or nanoparticle samples can be deposited onto a silicon wafer (thickness about 400 μm). Laser-induced acoustic desorption is used to desorb samples into the ion trap. In some embodiments, a frequency-doubled Nd:YAG (neodymium-doped yttrium aluminium garnet) laser beam (wavelength 532 nm, 30 mJ/pulse) with a pulse duration of approximately 6 ns was shone directly onto the back side of sample plate to desorb virus and nanoparticles by LIAD with a power density of around 10$^8$ W/cm2. The trapping radio-frequency (RF) voltage was set 1000 Vp-p (peak-to-peak voltage) approximately. The virus and nanoparticles released by laser desorption were trapped with an alternating-current (AC) field (ca. 2 kHz, depending on the particle size) and damped to the trap center by helium gas at about 60 mTorr.

Figure 6:
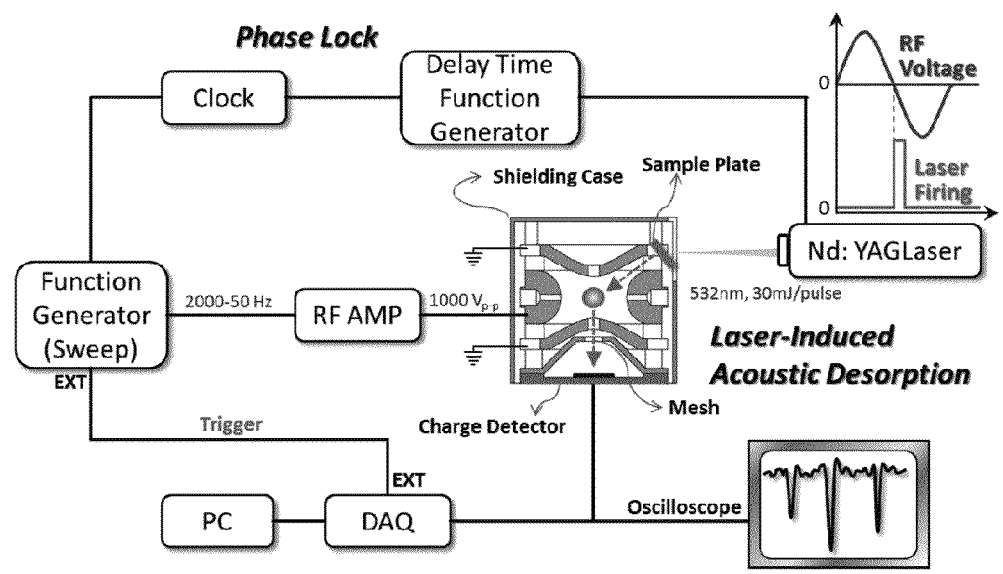
FIG. 6 shows a block diagram of an embodiment of a Virus Mass Spectrometer, including quadrupole ion trap, a pulsed Nd:YAG laser, a charge detector, a stainless steel shielding case, and an $SiO_2$ sample plate (400 nm thickness, high-resistance surface). An aliquot (10 μL) of the purified particles was placed on the front side of the sample plate. A frequency-doubled Nd:YAG laser beam (λ=532 nm, 30 mJ/pulse) with a pulse duration of approximately 6 ns was shone directly onto the back side of the sample plate. The laser firing is synchronized with the phase of RF for increasing the trapping efficiency.

FIG. 6 shows a block diagram of an embodiment of a Virus Mass Spectrometer, including quadrupole ion trap, a pulsed Nd:YAG laser, a charge sensitive detector, a stainless steel shielding case, and an $SiO_2$ sample plate (400 nm thickness, high-resistance surface). An aliquot (10 μL) of the purified particles was placed on the front side of the sample plate. A frequency-doubled Nd:YAG laser beam (λ=532 nm, 30 mJ/pulse) with a pulse duration of approximately 6 ns was shone directly onto the back side of the sample plate. The laser firing is synchronized with the phase of RF for increasing the trapping efficiency.

In one embodiment, a quadrupole ion trap was used to trap the desorbed and charged particles. The phase lock system to enhance trapping efficiency and collect more desorbed particles was used. The laser firing was synchronized with the zero radio frequency (rf) voltage by the four channel digital delay/pulse generator (Stanford Research System, Inc., model DG535, CA). With this approach, the analysis speed is increased by a factor of about 10. A shielding to the charge sensitive detector to reduce the electronic background. Desorption of nanoparticles and viruses without any matrix was done by laser induced acoustic desorption. Nanoparticle and virus samples were deposited onto a silicon wafer (thickness of approximately 400 μm). The laser was a frequency doubled Nd:YAG (neodymium-doped yttrium aluminum garnet) laser beam (wavelength 532 nm, 30 mJ/pulse, Laser Technique, Berlin, Germany) with a pulse duration of approximately 6 ns was shone directly onto the back side of the sample plate to desorb the nanoparticles/viruses by LIAD with a power density of approximately $10^8$ W/cm$^2$. The trapping rf voltage was set at 1000 Vp-p (peak-to-peak voltage) (TReK, Inc., model 5-80, NY). The nanoparticles and viruses released by laser desorption were trapped with an adjustable alternating-current (ac) field (about 2 kHz, depending on the particle size) and damped to the trap center by helium gas at about 60 mTorr to retard the kinetic energy of the desorbed particles for more efficient trapping. The ion trap was operated under an axial mass-selective instability mode by scanning the trapping frequency in the range 2000-200 Hz. A voltage of 1000 Vp-p was initially applied with a high-voltage transformer driven by an rf voltage power amplifier (TReK, Inc., model 5-80, NY) and a function generator (Stanford Research Systems, model DG345). The frequency was scanned with a functional generator so that particles with an unstable trajectory were ejected along the axial direction and subsequently detected by a charge detector. This instrument can rapidly measure the mass of a nanoparticle/virus and a microparticle/cell. On average, it takes less than 1 min to finish the measurement of one sample. Using this instrument, the speed of mass measurements for nanoparticles/viruses can be greatly increased relative to microscopy-based mass spectrometry.

EXAMPLE 7

Sample preparation. An aliquot (10 μL) of the purified particle suspension was deposited onto an about 400 μm thick silicon wafer and air-dried under a desiccated box. For the virus particle, lentiviruses were produced by co-transfecting a 15 cm dish, after additional purification by dialysis, were resuspended in filtered (0.2 μm pore size filter) deionized water at a concentration of about $1\times10^9$ particles/mL. The concentrations were $2\times10^{14}$ and $3\times10^{13}$ particles/mL, respectively. Polystyrene spheres were thoroughly washed with deionized water, recovered by centrifugation, and re-suspended in filtered (0.2 μm pore size filter) distilled water. The purification approach reduced the presence of sodium azide or any residual salt components that could inadvertently produce background particles during laser desorption.

In one embodiment, an aliquot (10 μL) of the purified particle suspension was deposited onto a about 400-μm-thick silicon wafer and then air dried in a desiccation box. The standards were spherical polystyrene nanoparticles with sizes of 50, 10, and 900 nm, which were purchased from Thermo Scientific (Fremont, Calif.). The concentrations were $2\times10^{14}$, $3\times10^{13}$, and $5\times10^{10}$ particles/mL, respectively. Polystyrene spheres were thoroughly washed with deionized water, recovered by centrifugation, and resuspended in filtered (0.2-μm pore size filter) and distilled water. The purification process is important because the presence of sodium azide or any residual salt could produce background particles during laser desorption, rendering the analysis difficulty. For the virus particle, lentiviruses were produced by cotransfecting a 15-cm dish, followed by additional purification with dialysis. Then, the viruses were resuspended in filtered (0.2-μm pore size filter) and deionized water at a concentration of approximately $1\times10^9$ particles/mL. The viruses were concentrated by ultracentrifugation (36 mL/tube, 25 000 rpm, 1.5 h, 4° C., low brake, SW28 rotor). The minimal packaging G glycoprotein of the vesicular stomatitis virus (VSV-G) with pseudotyped lentiviral vector has been adopted to increase vector biosafety. An important approach for alleviating such concerns is the use of self-inactivating transfer vectors. These vectors contain a deletion in the downstream long terminal repeat (LTR) that when transduced into target cells result in the transcriptional inactivation of the upstream LTR and substantially diminish the risk of vector mobilization and recombination.

Figure 7:
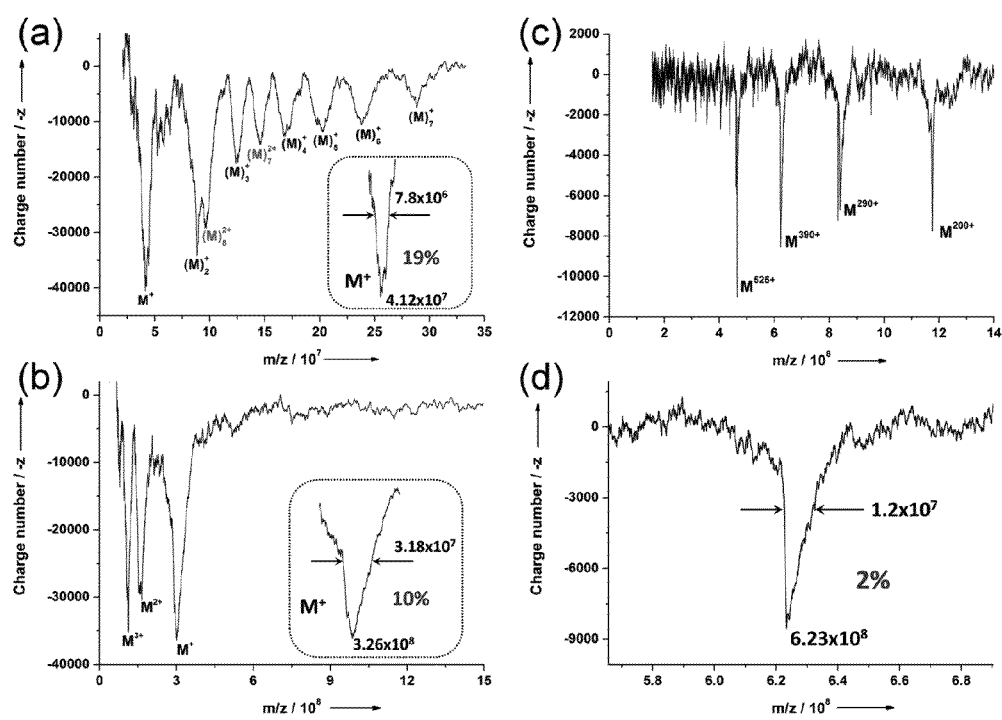
FIG. 7 shows mass spectra of 50, 100, and 900 nm polystyrene spherical particles obtained with an embodiment of a Virus Mass Spectrometer. The typical trapping parameters (Ω/2π and Vp-p) used in each measurement were (a) 2000 Hz and 1000 V for particles of 50 nm, (b) 1500 Hz and 1000 V for particles of 100 nm, (c) 800 Hz and 1500 V for particles of 900 nm, (d) the mass distribution was approximately 2% (ΔM/M) of 900 nm. Since the mass distributions for the inserts in FIG. 7a and FIG. 7b are significantly higher than 2%, they should reflect the mass distributions of the particles in the samples. All of the mass spectra were the sum of twenty individual single-scan mass spectra. 900-nm polystyrene particle sample was with a narrow diameter distribution of about 0.5% given by the manufacturer. The mass distribution was measured to be approximately 2% (ΔM/M). Therefore, the resolution is approximately 50 for this embodiment of a VMS instrument.

FIG. 7 shows mass spectra of 50, 100, and 900 nm polystyrene spherical particles obtained with an embodiment of a Virus Mass Spectrometer. The typical trapping parameters (Ω/2π and Vp-p) used in each measurement were FIG. 7a, 2000 Hz and 1000 V for particles of 50 nm, FIG. 7b, 1500 Hz and 1000 V for particles of 100 nm, FIG. 7c, 800 Hz and 1500 V for particles of 900 nm, FIG. 7d, the mass distribution was approximately 2% (ΔM/M) of 900 nm. Since the mass distributions for the inserts in FIG. 7a and FIG. 7b are significantly higher than 2%, they should reflect the mass distributions of the particles in the samples. All of the mass spectra were the sum of twenty individual single-scan mass spectra. 900-nm polystyrene particle sample was with a narrow diameter distribution of about 0.5% given by the manufacturer. The mass distribution was measured to be approximately 2% (ΔM/M). Therefore, the resolution is approximately 50 for this embodiment of a VMS instrument.

EXAMPLE 8

RF Synchronization. Referring to the timing diagram of FIG. 8, ions are in general not trapped when the laser is fired on the 90 degree phase of the trapping RF. As shown in the calculation of FIG. 9a, few ions enter and are held in the trap when the laser is fired at the 90 degree phase position. Under this condition, the ions can be repelled to the end cap.

Referring to the timing diagram of FIG. 8, many ions are trapped when the laser is fired on the 0 degree phase of the trapping RF. As shown in the calculation of FIG. 9b, many ions enter and are held in the trap when the laser is fired at the 0 degree phase position. Under this condition, the ions can pass through the gap to the center of the ion trap.

Referring to the timing diagram FIG. 8, ions are in general not trapped when the laser is fired on the 270 degree phase of the trapping RF. As shown in the calculation of FIG. 9c, few ions enter the trap when the laser is fired at the 270 degree phase position. Under this condition, the ions can be repelled to the end cap. Ions already in the trap can be maintained in a trapped state.

Thus, the synchronization of the laser firing to the trapping RF increases the number of ions that enter the trap. This method has been found to provide an unexpectedly advantageous increase in the signal-to-noise level of analyte detection.

In further aspects, the synchronization of the trapping RF to the axial RF can increase the resolution of m/z in the mass spectrum that can be obtained. Referring to the timing diagram of FIG. 10, the synchronization of the trapping RF to the axial RF is demonstrated.

Referring to FIG. 11, the mass spectrum of C60 nanoparticles is shown. The expansion of the region where the main peak was observed shows that m/z 720 was detected, along with m/z 721 and m/z 722.

Referring to FIG. 12, the timing for laser firing is shown. An adjustable firing time can be set for synchronizing the laser firing to the trapping RF. The laser fires on the leading edge of a TTL pulse, when the RF voltage is low, or close to zero. In some embodiments, the laser can be fired multiple times during the trapping period.

Referring to FIG. 12, the timing for frequency sweeping and signal acquisition is shown. In certain embodiments, the trapping RF and axial RF are synchronized to start from phase 0. In some embodiments, when the trapping RF and axial RF are synchronized, ions of a particular m/z can be ejected from the trap over a narrower range of time, as compared to a non-synchronized acquisition. Thus, the apparatus and method of this invention can increase the resolution by decreasing ΔM.

Referring to FIG. 12, the timing protocol can be set as follows:

Set Ch1, trapping frequency, amplitude, sweep start frequency and end frequency, delta frequency;

Set Ch2, axial frequency/n, (n: 2, 3, 4 . . . ), amplitude, sweep start frequency/n and end frequency/n, phase 0;

Set Ch3, axial frequency/n, (n: 2, 3, 4 . . . ), amplitude, sweep start frequency/n and end frequency/n, phase 180.

The VMS apparatus further includes a non-transient computer readable storage medium containing instructions for carrying out a method for performing mass spectrometry of a nanoparticle analyte. The non-transient computer readable storage medium can be a disk, a hard disk, a flash memory device, RAM memory, computer memory, a magnetic tape or disk, a DVD, a CD, a DVD R, a DVD RW, a CD R, or a CD RW.

All publications and patents and literature specifically mentioned herein are incorporated by reference for all purposes.

It is understood that this invention is not limited to the particular methodology, protocols, materials, and reagents described, as these may vary. It is also to be understood that the terminology used herein is for the purpose of describing particular embodiments only, and is not intended to limit the scope of the present invention which will be encompassed by the appended claims.

It must be noted that as used herein and in the appended claims, the singular forms "a", "an", and "the" include plural reference unless the context clearly dictates otherwise. As well, the terms "a" (or "an"), "one or more" and "at least one" can be used interchangeably herein. It is also to be noted that the terms "comprises," "comprising", "containing," "including", and "having" can be used interchangeably.

Without further elaboration, it is believed that one skilled in the art can, based on the above description, utilize the present invention to its fullest extent. The following specific embodiments are, therefore, to be construed as merely illustrative, and not limitative of the remainder of the disclosure in any way whatsoever.

All of the features disclosed in this specification may be combined in any combination. Each feature disclosed in this specification may be replaced by an alternative feature serving the same, equivalent, or similar purpose.

What is claimed is:

1. An apparatus for mass spectrometry comprising:
    a desorption plate;
    a laser for firing a beam to impinge upon the desorption plate;
    a mass analyzer for measuring mass over the range of m/z from $10^5$ to $10^{10}$ using applied trapping RF and axial RF voltages, wherein the mass analyzer is a quadrupole ion trap having a ring electrode and first and second end cap electrodes, wherein the ring electrode is spaced apart by a gap from the first end cap electrode, and wherein the desorption plate is adjacent to the gap;
    an electrical shield surrounding the mass analyzer;
    a charge sensitive detector, wherein the electrical shield electrically isolates the mass analyzer from the charge sensitive detector; and
    a synchronizer for phase locking the laser firing to the applied trapping RF.

2. The apparatus of claim 1, wherein a trapping RF is applied to the ring electrode, and an axial RF is applied to the end cap electrodes, and wherein the phase of the trapping RF is synchronized to the phase of the axial RF.

3. The apparatus of claim 1, wherein the resolution of a mass spectrum of nanoparticles obtained with the apparatus is at least 50.

4. The apparatus of claim 1, wherein the laser fires when the applied radiofrequency voltage amplitude is less than one volt.

5. The apparatus of claim 1, wherein the laser fires when the applied radiofrequency voltage amplitude is zero.

6. The apparatus of claim 1, wherein the desorption plate is a laser induced acoustic desorption plate.

7. The apparatus of claim 1, wherein the mass analyzer is a quadrupole ion trap.

8. The apparatus of claim 1, wherein the applied radiofrequency voltages are applied at a trap driving frequency in the range 200-2000 Hz.

9. The apparatus of claim 1, wherein the applied radiofrequency voltages are in the range zero to 3000 Vp-p.

10. The apparatus of claim 1, wherein the electrical shield is stainless steel.

11. A method for performing mass spectrometry of a nanoparticle analyte ion, the method comprising:
    desorbing the nanoparticle analyte ion from an acoustic desorption plate by firing a laser to impinge upon the desorption plate;
    trapping the nanoparticle analyte ion in a mass analyzer configured to measure mass over the range of m/z from $10^5$ to $10^{10}$ using applied trapping RF and axial RF voltages, wherein the mass analyzer is a quadrupole ion trap having a ring electrode and first and second end cap electrodes, wherein the ring electrode is spaced apart by a gap from the first end cap electrode, and wherein the desorption plate is adjacent to the gap; and
    detecting the charge of the nanoparticle analyte, wherein an electrical shield electrically isolates the mass analyzer from the detector, thereby obtaining a mass spectrum of the analyte;

and wherein the laser firing is phase lock synchronized to the applied trapping RF.

12. The method of claim 11, the method further comprising
applying a trapping RF to the ring electrode and an axial RF to the end cap electrodes; and
synchronizing the phase of the trapping RF to the phase of the axial RF.

13. The method of claim 11, further comprising adjusting the phase of the RF at which the laser is fired, thereby increasing the signal to noise.

14. The method of claim 11, wherein the laser fires when the applied radiofrequency voltage amplitude is less than one volt.

15. The method of claim 11, wherein the laser fires when the applied radiofrequency voltage amplitude is zero.

16. The method of claim 11, wherein the signal to noise of the mass spectrum is increased at least two-fold compared to a device that does not have phase synchronized laser firing.

17. The method of claim 11, wherein the nanoparticles are viruses.

18. The method of claim 11, wherein the nanoparticles are single whole viruses.

19. The method of claim 11, wherein the nanoparticles are virions.

20. The method of claim 11, wherein the nanoparticles are nanorods, quantum dots, liposomes, or multiple layers of nanoparticles.

21. The method of claim 11, wherein the nanoparticles are human immunodeficiency virus, flu virus, or SARS virus.

22. The method of claim 11, wherein the mass distribution of the nanoparticles is determined.

23. The method of claim 11, further comprising matching the peaks in the mass spectrum of the nanoparticles with different charges and/or clusters with different numbers of charge.

24. The method of claim 11, further comprising determining the kinds of viruses present in a sample based on mass measurements.

25. A non-transient computer readable storage medium containing instructions for carrying out a method for performing mass spectrometry of a nanoparticle analyte ion, the method comprising:
desorbing the nanoparticle analyte ion from an acoustic desorption plate by firing a laser to impinge upon the desorption plate;
trapping the nanoparticle analyte ion in a mass analyzer configured to measure mass over the range of m/z from $10^5$ to $10^{10}$ using applied radiofrequency voltages, wherein the mass analyzer is a quadrupole ion trap having a ring electrode and first and second end cap electrodes, wherein the ring electrode is spaced apart by a gap from the first end cap electrode, and wherein the desorption plate is adjacent to the gap; and
detecting the charge of the nanoparticle analyte, wherein an electrical shield electrically isolates the mass analyzer from the detector;
and wherein the laser firing is phase lock synchronized to the applied radiofrequency voltages.

26. The non-transient computer readable storage medium of claim 25, the method further comprising
applying a trapping RF to the ring electrode and an axial RF to the end cap electrodes; and
synchronizing the phase of the trapping RF to the phase of the axial RF.

* * * * *